United States Patent [19]
Devauchelle et al.

[11] Patent Number: 5,939,285
[45] Date of Patent: Aug. 17, 1999

[54] METHOD FOR REGULATING THE EXPRESSION OF A GENE IN A BACULOVIRUS USING A RETINOIC ACID RECEPTOR BINDING SITE AND VECTOR THEREFOR

[75] Inventors: Gérard Devauchelle, Saint-Christol-les-Aleès; Marie-Hélène Ogliastro, Alès; Martine Cerutti, Saint-Christol-les-Alès, all of France

[73] Assignees: Institut National de la Recherche Scientifique Agronomique (INRA), Paris Cedex, France; Centre National de la Recherche Scientifique (CNRS), Paris Cedex, France

[21] Appl. No.: 08/913,617

[22] PCT Filed: Mar. 22, 1996

[86] PCT No.: PCT/FR96/22437

§ 371 Date: Dec. 18, 1997

§ 102(e) Date: Dec. 18, 1997

[87] PCT Pub. No.: WO96/29400

PCT Pub. Date: Sep. 26, 1996

[30] Foreign Application Priority Data

Mar. 23, 1995 [FR] France .................................. 95/03412

[51] Int. Cl.⁶ ............................ C12P 21/00; C12N 15/86; C12N 15/63
[52] U.S. Cl. ..................... 435/69.1; 435/320.1; 435/455; 435/456; 435/463; 435/466
[58] Field of Search ............................... 435/69.1, 172.1, 435/172.3, 320.1, 455, 456, 463, 466

[56] References Cited

FOREIGN PATENT DOCUMENTS

| | | |
|---|---|---|
| 325849 | 8/1989 | European Pat. Off. . |
| WO 89/12687 | 12/1989 | WIPO . |
| WO 91/07488 | 5/1991 | WIPO . |
| WO 91/14695 | 10/1991 | WIPO . |

*Primary Examiner*—David Guzo
*Attorney, Agent, or Firm*—Oblon, Spivak, McClelland, Maier & Neustadt, P.C.

[57] ABSTRACT

A recombinant vector useful for regulating the expression of a gene controlled by a baculovirus polyhedrin promoter or P10 promoter, via a sequence forming an RAR-type hormone receptor binding site.

14 Claims, 4 Drawing Sheets

ATC ATG TCA AAG  →  ATC Agc TgA AAC

SEQUENCE LISTING

<160> NUMBER OF SEQ ID NOS: 3

<210> SEQ ID NO 1
<211> LENGTH: 9
<212> TYPE: DNA
<213> ORGANISM: Artificial Sequence
<220> FEATURE:
<223> OTHER INFORMATION: Description of Artificial
Sequence:Promoter
      sequence; n is A or C or G
or T

<400> SEQUENCE: 1 gttgannng

9

<210> SEQ ID NO 2
<211> LENGTH: 14
<212> TYPE: DNA
<213> ORGANISM: Artificial Sequence
<220> FEATURE:
<223> OTHER INFORMATION: Description of Artificial
Sequence:Promoter
      sequence

<400> SEQUENCE: 2
gttgacagtg ttca

14

<210> SEQ ID NO 3
<211> LENGTH: 14
<212> TYPE: DNA
<213> ORGANISM: Artificial Sequence
<220> FEATURE:
<223> OTHER INFORMATION: Description of Artificial
Sequence:Promoter
      sequence; n is A or C or G
or T

<400> SEQUENCE: 3
gttgannnng ttca

14

METHOD FOR REGULATING THE EXPRESSION OF A GENE IN A BACULOVIRUS USING A RETINOIC ACID RECEPTOR BINDING SITE AND VECTOR THEREFOR

BACKGROUND OF THE INVENTION

Field of the Invention

The present invention relates to new expression vectors obtained from baculoviruses.

DESCRIPTION OF THE BACKGROUND

The baculoviruses, represented by the *Autographa californica* nuclear polyhedrosis virus (AcMNPV), possess several promoters which are active in different phases of the viral replication cycle. Some of these promoters are used in genetic engineering to control the expression of heterologous genes inserted into the baculovirus genome. Among the ones most commonly employed, two strong very late promoters may be mentioned: the polyhedrin (polh) promoter and the P10 polypeptide promoter, which are active only at the end of the infectious cycle, after replication of the viral genome, and which enable the genes placed under their control to be expressed at a high level.

The polh and P10 promoters are described in detail in the following publications: POSSEE and HOWARD [Nucleic Acid Research, vol. 15, pp. 10233–10248 (1987)] for the polyhedrin promoter, and QIN et al. [J. Gen. Virol. vol. 70, pp. 1273–1279, (1989)] for the P10 promoter. The sequence localized between positions (−71 and +1) defined relative to the A(+1) of the polyhedrin ATG is generally defined as the "polyhedrin promoter", and the sequence localized between positions (−70 and +1) defined relative to the A(+1) of the p10 polypeptide ATG is generally defined as the "p10 promoter".

The obtaining from a baculovirus, of a vector expressing a foreign gene under transcriptional control of a promoter of the baculovirus, is generally performed by methods known per se, through construction of a transfer vector containing the the promoter, then recombination with the DNA of the wild-type virus, and lastly selection of the recombinants.

SUMMARY OF THE INVENTION

During the replication cycle of the baculovirus, the early genes are expressed first: the transcription of these genes involves the host cell's RNA polymerase II.

Subsequently, the late and very late genes such as polh and P10 are transcribed by a particular RNA polymerase, of at least partially viral origin, which is insensitive to α-amanitin.

An A/GTAAG motif common to all the late genes constitutes the transcription startsite. This motif is essential for the recognition of these promoters by the RNA polymerase, and hence for their activity. The mechanisms which govern the transcriptional activation are not yet, however, precisely known.

Previous work of the inventors' team has shown that it is especially advantageous, in order to increase the level of expression of a heterologous gene placed under the control of one of the two strong very late promoters polh or P10, to construct a baculovirus in which only one of these two strong late promoters is inactivated, and to cause the said gene to be expressed under the control of the remaining promoter.

This principle has been used as a basis for the construction of several modified baculoviruses [European Application No. 91 913 605.1 in the names of the INSTITUT NATIONAL DE LA RECHERCHE AGRONOMIQUE (I.N.R.A.) and of the CENTRE NATIONAL DE LA RECHERCHE SCIENTIFIQUE (C.N.R.S.); CHAABIHI et al., J. Virol., 67, 2664–2671 (1993)], in which either the P10 promoter (baculovirus designated AcSLP33, for example) or the polyhedrin promoter (baculovirus designated AcSLP10, for example) is inactivated by deletion.

In the context of continuing their work on the regulation of expression in baculoviruses, it occurred to the inventors to study the influence of the coding sequence of the P10 gene on the expression of the latter. For this purpose, they made, from the wild-type baculovirus AcMNPV, constructs comprising the CAT reporter gene inserted at one of the positions +16, +150 or +230 of the sequence coding for 10 (these positions are defined relative to the A (+1) of the ATG initiation codon of P10), and studied the simultaneous expression of the CAT reporter gene and of the polyhedrin gene in the recombinant viruses obtained (designated AcCAT+16, AcCAT+150 and AcCAT+230, respectively), relative to the wild-type baculovirus AcMNPV and to the modified baculovirus AcSLP33 (in which the P10 promoter is inactivated).

The recombinant viruses AcCAT+16, AcCAT+150 and AcCAT+230 are shown diagrammatically in FIG. 1.

This allowed the inventors to notice that when the reporter gene is inserted at +16 (this insertion is accompanied by the deletion of a portion of the sequence coding for P10), the expression of the reporter gene is weak, while the expression of the polyhedrin gene increases very significantly although the P10 promoter is intact, until reach a level comparable to the one observed in a virus in which the P10 promoter is inactivated, such as the virus AcSLP33.

In contrast, when the reporter gene is inserted further downstream (+150 or +230), the expression of the said gene increases, and that of polyhedrin decreases to return to a baseline level comparable to that observed in the wild-type baculovirus AcMNPV.

Moreover, during other investigations under taken independently, the inventors sought to express the α and γ isoforms of the human retinoic acid receptor (hRAR) in insect cells, and constructed for this purpose, from wild-type AcMNPV baculoviruses, recombinant baculoviruses which express the said α or γ iso-forms, respectively, under the control of the polyhedrin promoter. Now, during these investigations, they observed an unexpected overexpression of the P10 gene in these baculoviruses.

This activation is revealed by the mRNA level which is twice as high as the control (consisting of the wild-type baculovirus AcMNPV) in the case of the α receptor, and 5 times as high in the case of the γ receptor: the activation is hence taking place at the transcriptional level.

Moreover, this activation is observed not only during the transfection of a cell with a double-recombinant virus, but also during the cotransfection of a cell with two plasmids (one expressing an RAR and the other carrying an RARE domain localized in the P10 gene); the activation is hence a trans-activation.

The inventors established a parallel between the results of the two series of investigations reported above, and went on to analyse the sequence of the P10 region in order to look for the possible existence of sequences related to the ones constituting binding sites for nuclear receptors, and especially for retinoic receptors.

The retinoic acid receptors (RARs) belong to the family of "nuclear receptors" which also comprises, for example, in vertebrates, the vitamin D3 receptors or the thyroid receptors. Other receptors, designated RXRs and which are, like the RARs, activated by retinoic acid or by other retinoids, have also been described.

Nuclear receptors are known to be capable of activating the transcription of a target gene. This activation involves, on the one hand the binding of these nuclear receptors to their specific ligand, and on the other hand their binding to DNA, which involves the recognition of short consensus DNA sequences known as "response elements" generally situated upstream of the target gene. The RARs and RXRs thus recognize consensus sequences which are repeated once or several times, in tandem or palindromically, and define portions of DNA known as RARE or RXRE elements, respectively [GORDMAN et al. Mol. Cell. Biol. 2, 1044–1051 (1982)]. Various consensus sequences have been identified. For example, the response elements for the RARβ receptor, which are described in Application PCT W091/07488, comprise tandem repeats of the sequence GTTCAC; Application PCT WO 92/16658 describes RXRE response elements, and especially an RXRE element obtained from the promoter of the rat CRBPII gene, which comprises tandem repeats of the sequence AGGTCA.

The response elements for the nuclear receptors have a variable specificity. Some, like the thyroid hormone receptor response element (TRE), respond not only so their own receptor but also to FARs and to RXRs. Others are more specific, like the PARβ receptor response elements which respond only weakly to RXRs. Others, like the RXRE element which is described in Application PCT WO 92/16658, can bind RAR or RXR receptors, but only the latter produce a response which brings about the activation of the promoter placed downstream of this RXRE element. This trans-activation by RXRs is blocked in the presence of RARs.

In insects, there are also proteins akin to RARs; particular examples are the hormone receptor for ecdysone (EcR) and for the USP protein of Drosophila. Application PCT WO 92/14695 describes an RXR type receptor, designated XR2C, obtained from Drosophila.

The proposal has been made to place response elements for RARs or for RXRs upstream of the promoter of a gene, at a distance from the said promoter of between 30 bp and 10,000 bp, so as to obtain the activation of the said gene via RAR or RXR receptors expressed in the same cell. For example, Application P4T WO 91/07488 proposes the use of RARP receptor response elements for activating the transcription of genes in mammalian cells. Application PCT WO 92/16658 proposes the use of the RXRE response elements which it describes for studying the trans-activation of genes by RXR receptors, and the blocking of this transactivation in the presence of XRA receptors in mammalian, bird or insect cells. Application PCT WO 92/14695 mentions several response elements which are considered to be usable with the XR2C receptor; in fact, it describes the use of this receptor only with a TRE response element placed upstream of the ADH promoter of Drosophiia.

Analysis of the sequence of the P10 region, performed by the inventors, revealed the existence in the P10 gene of an intragenic sequence GTTGACAGTGTTCA (SEQ ID NO:2), similar to a consensus sequence recognized by RARs and hence constituting a putative RARE element. This sequence is localized, in wild-type AcMNPV, at position +61 relative to the A(+1) of the ATG initiation codon of P10.

Further experiments performed by the inventors have enabled it to be shown that activation of the P10 gene, or of a reporter gene placed under the transcriptional control of the P10 promoter, in the presence of the product of an RAR gene placed under the control of the polyhedrin promoter, takes place on condition that the RARE type domain localized in the P10 gene is present. In addition, this activation also takes place when the RARE type domain is removed from its initial position and put back in another position in proximity to the P10 promoter, downstream or upstream of this promoter. Lastly, if the RARE type domain is placed in the same manner in proximity to another promoter, the activation of this other promoter is observed. In all cases, this RARE element is active irrespective of whether it i placed upstream or downstream of the promoter, and regardless of its orientation with respect to the latter.

Analysis of the sequence of the P10 gene in the baculoviruses *Choristoneura fumiferana* NPV and *Bombyx mori* NPV reveals the conservation of the RARE motif. Hence these baculoviruses can, on the same basis as AcMNPV, be used for carrying out the present invention.

The finding by the inventors of the RARE-like intragenic sequence and of its effective role in the regulation of the expression of the P10 gene allow to provide new means of regulating the expression of heterologous genes coding for proteins of interest under the control of baculovirus promoters.

The present invention relates to these means of regulation, which include several variants.

According to a first variant of the invention, the activation of a baculovirus promoter in a host cell, especially of a strong late promoter such as the P10 or polh promoter, is obtained in the presence of the product of an RAR gene in the same host cell, and of an RARE type sequence situated in cis and in proximity to the said baculovirus promoter.

For the purposes of the present invention an RARE sequence is considered to be "in proximity to a promoter" if it [lacuna] situated downstream or upstream of the said promoter at a distance of between 10 and 10,000 bp, and preferably less than 1000 bp, from the transcription startsite of the said promoter.

The subject of the present invention is a method for regulating the expression of a gene placed under the transcriptional control of a baculovirus promoter in an expression vector comprising an RARE type sequence situated in proximity to the said baculovirus promoter, which method is characterized in that the expression of the said gene is effected in the presence of the translation product of a gene coding for an RAR type hormone receptor.

DETAILED DESCRIPTION OF THE INVENTION

Figure 1:
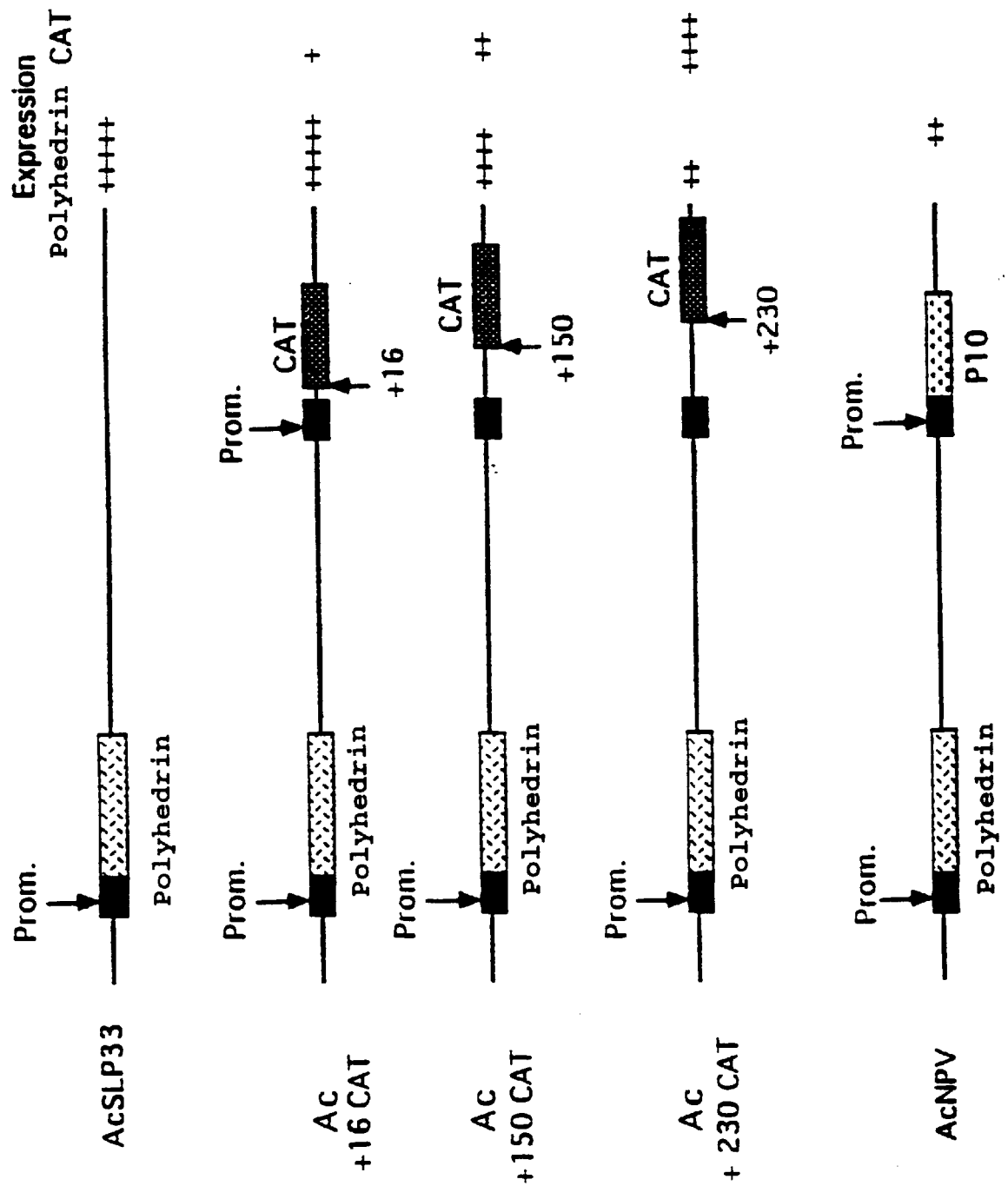
FIG. 1: illustration of transfer vectors.

The baculovirus promoter can be, for example, the P10 promoter, the polh promoter, one of the promoters of the IE1 and IEN genes or a synthetic cromoter. Advantageously, it is a strong late promoter such as the P10 promoter or the polh promoter.

Preferably, the PAR type hormone receptor is an RARα receptor, an RARβ receptor or an RARγ receptor, and the RARE DNA sequence is a sequence (identified in the attached sequence listing under the number SEQ ID NO: 1) corresponding to the general formula GTTGANNNNGTTCA(SEQ ID NO:3) where N represents A or C or G or T, and especially the sequence GTTGA-CAGTGTTCA identified in the attached sequence listing under the number SEQ ID NO: 2.

According to a preferred embodiment of a method according to the invention, the expression of the gene placed under the transcriptional control of the said baculovirus promoter is effected in the presence, in the same cell, of a gene expressing an RAR type hormone receptor.

The baculovirus promoter and the gene expressing an PAR type hormone receptor can be carried by the same DNA molecule, or alternatively by two different DNA molecules.

The gene expressing an PAR type hormone receptor may be placed under the control of any promoter, provided the said promoter is expressed in the host cell. Advantageously, it is placed under the control of a second baculovirus promoter; this second promoter and the one under the control of which the gene of interest is expressed may be identical or different.

To carry out a method according to the invention, it is possible, for example, to use expression vectors, known per se, which do not carry a gene expressing an RAR type hormone receptor, and which comprise at least the portion of the P10 gene consisting of the promoter of the said gene followed by the sequence portion coding for the P10 protein which comprises the sequence GTTGACAGTGTTCA(SEQ ID NO:2), the said promoter and said coding sequence being arranged in a manner identical to their arrangement in the wild-type P10 gene. These vectors can be used in the presence, in the same host cell, of another DNA molecule expressing an RAR type hormone receptor.

New recombinant vectors, which form part of the subject of the present invention, can also be used.

Recombinant vectors according to the invention, which can be used for carrying out a method in which the baculovirus promoter and the gene expressing an RAR type hormone receptor are carried by two DNA molecules, consist of recombinant baculoviruses comprising a DNA sequence constituting an RAR type hormone receptor binding site, placed in proximity to a baculovirus promoter under the control of which it is desired to express a gene coding for a protein of interest, on condition that, if the baculovirus promoter is the P10 promoter and the RARE sequence is the sequence GTTGACAGTGTTCA(SEQ ID NO:2), the said sequence is situated relative to the said promoter in a different location from the one it occupies in the wild-type P10 gene, or is separated from the said promoter by a sequence different from the one which separates it from the wild-type P10 promoter.

GTTGACAGTCTTCA(SEQ ID NO:2) the said sequence is situated relative to the said promoter in a different location from the one it occupies in the wild-type P10 gene, or is separated from the said promoter by a sequence different from the one which separates it from the wild-type P10 promoter.

Other recombinant vectors according to the invention, which can be used for carrying out a method in which the baculovirus promoter and the gene expressing an RAR type hormone receptor are carried by the same DNA molecule, consist of recombinant baculoviruses comprising an RARE DNA sequence constituting an RAR type hormone receptor binding site, placed in proximity to a first baculovirus promoter under the control of which it is desired to express a gene coding for a protein of interest, and a DNA sequence coding for an PAR type hormone receptor, placed under the transcriptional control of a second baculovirus promoter.

The first and the second promoter can, for example, be the P10 promoter, the polh promoter, the promoters of the IE1 and IEN genes or synthetic promoters. A copy of the first promoter can also be used as second promoter.

Advantageously, the first promoter is the P10 promoter and the second promoter the polh promoter, or alternatively a second copy of the P10 promoter. Advantageously also, the first promoter is the polh promoter and the second promoter the P10 promoter, or alternatively a second copy of the polh promoter.

Preferably, the RAR type hormone receptor is an RARα receptor, an RARβ receptor or an RARγ receptor, and the RARE DNA sequence is a sequence as defined in the attached sequence listing under the number SEQ ID NO:1 or SEQ ID NO:2.

Advantageously, the RARE DNA sequence is placed downstream of the first promoter.

According to a preferred embodiment, these vectors comprise, in addition, at least one heterologous sequence coding for the protein of interest which it is desired to express, placed under the transcriptional control of the first promoter, or at least one site for insertion of the said sequence.

Vectors according to the invention are, for example, the double-recombinant viruses obtained from the recombinant viruses Ac+150 and Ac+230, described above, by insertion of a gene coding for one of the retinoic acid receptors RARα or RARγ, under the control of the polyhedrin promoter.

According to a second variant of the invention, an activation of the polh promoter similar to that observed in expression vectors in which the P10 promoter is inactivated is obtained using expression vectors bereft of the whole of the sequence coding for the P10 protein.

In accordance with this second variant, the subject of the present invention is recombinant vectors which can be used to increase the expression of a gene under the transcriptional control of the baculovirus polyhedrin promoter, and which consist of modified baculoviruses comprising a polyhedrin promoter and a P10 promoter which are intact and functional, and in which the region in the vicinity of the P10 is bereft of any sequence constituting an RAR type hormone receptor binding site.

According to a preferred embodiment of the vectors according to this second variant of the invention, they are bereft of the whole of the sequence coding for the P10 protein.

According to another preferred embodiment of the vectors according to this variant of the invention, they comprise, in addition, at least one sequence coding for a heterologous protein which it is desired to express, placed under the transcriptional control of a polyhedrin promoter, or at least one site for insertion of the said sequence.

Vectors according to this second variant of the invention can, for example, be obtained from an Ac+16 recombinant virus.

According to another preferred embodiment of the vectors according to this second variant of the invention, they comprise, in addition, a DNA sequence coding for an RAR type hormone receptor, which sequence is placed under the transcriptional control of a baculovirus promoter other than the P10 promoter.

In effect, the inventors observed that, when a gene (such as, for example, the CAT reporter gene) is inserted under the transcriptional control of the P10 promoter, and in the absence of the RARE sequence, not only is an absence of activation noted, but even an inhibition of its expression during coexpression with RARs.

Vectors of this type may be obtained from Ac+16 by insertion of a gene coding for one of the retinoic acid receptors RARα or RARγ, under the control of the polyhedrin promoter; [sic]

Vectors according to the invention can constitute transfer vectors or expression vectors. They may be obtained from any baculovirus or construct (such as a transfer vector) derived from baculoviruses, on condition that the said baculovirus or said construct comprises sequences constituting the P10 promoter as are defined above.

A better understanding of the present invention will be gained from the further description which follows, which relates to examples of construction and of use of expression vectors according to the invention.

It should, however, be clearly understood that these examples are given only by way of illustration of the subject of the invention and in no way constitute a limitation of the latter.

The protocols used in the examples which follow make use of standard techniques of genetic engineering, such as the ones described by SAMBROOK et al. [Molecular cloning: A Laboratory Manual; Second Edition, Cold Spring Harbor Laboratory, 1989], or by O'REILLY et al. [Baculovirus Expression Vectors: A Laboratory Manual; Freeman and Co., New York, (1992)], for the manipulation of baculovirus DNA. The conditions distinctive to each experiment are, if necessary, specified in the corresponding examples.

EXAMPLE 1

1) Plasmid DNAs and transfer vectors

A series of three transfer vectors, designated pMH16, pMH150 and pMH230, respectively, was constructed in order to introduce the bacterial gene coding for CAT (chloramphenicol acetyltransferase) into the sequence coding for P10, at positions +16, +150 and +230.

Figure 2:
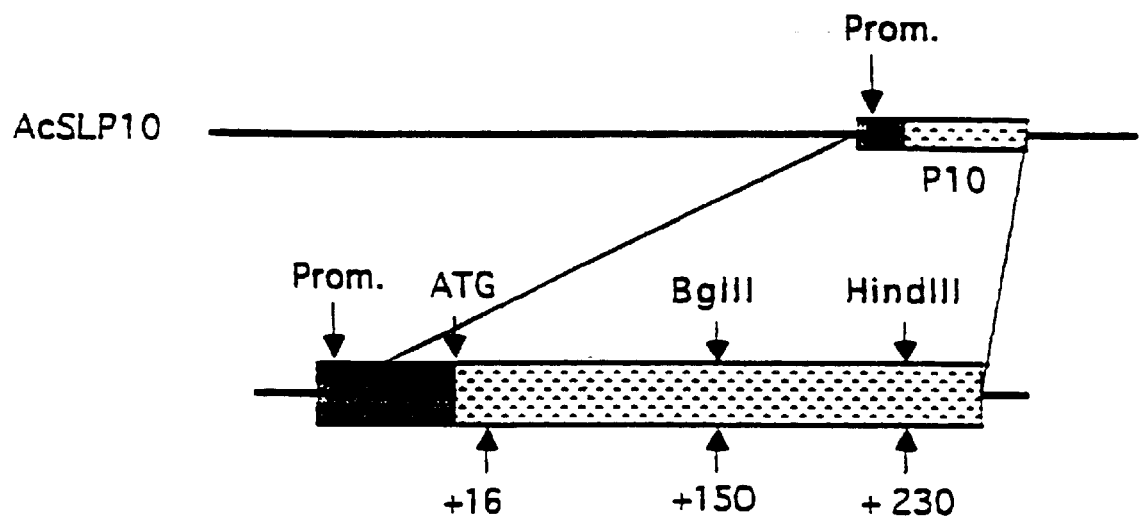
FIG. 2: a map of the p10 region.
Figure 2:
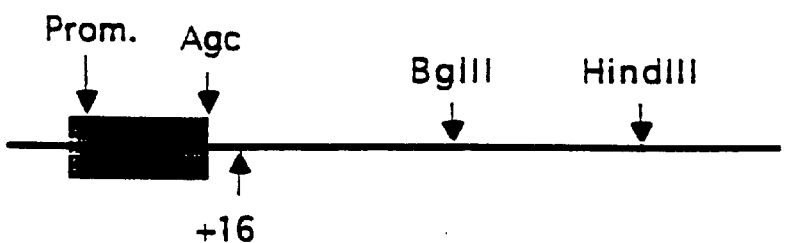

FIG. 2 depicts a map of the P10 region, showing the positions in question.

In these three constructions, the ATG codon of P10 has been mutated to AGC, and a PvuII restriction site was created (sequence ATG TCA mutated to AGC TGA).

pMH16

The plasmid pMH16 is derived from the transfer vector pGm16. The vector pGm16 contains an insert obtained from the EcoRI-P fragment of the baculovirus GmMNPV, mutated as indicated above at the translation initiation site of P10, and in which the sequence included between the bases +16 and +265 of the P10 gene has been deleted and replaced by a BglII linker.

To obtain pMH16, a 1900 bp HindIII-NsiI fragment isolated from the HindIII-Q fragment of AcMNPV, which contain the hr5 sequences and the p26 gene, was introduced between the HindIII and NsiI sites of pGm16.

The 790-bp BglII-BanI fragment obtained from the plasmid pBLCAT2 (LUCKOW and SCHUTZ, Nucleic Acid Res., 15, (13) 5940 (1987) [lacuna] and comprising the sequence coding for CAT was then introduced into the plasmid at the BglII site.

pMH150 and pMH230

The plasmids pMH150 and pMH230 are derived from the same construct, which was made by inserting a 1900-bp NsiI-EcoRI fragment carrying mutations indicated above of the EcoRI-P fragment of AcMNPV between the NsiI and KpnI sites of the HindIII-Q fragment of AcMNPV, previously cloned to the vector pUC18.

To obtain plasmid pMH15O, the BglII-BanI fragment of pBLCAT2 comprising the sequence coding for CAT was introduced at the BglII site situated at position +150 in the sequence coding for P10. To obtain plasmid pMH230, the said BglII-BanI fragment was introduced at the HindIII site situated at position +230 in the sequence coding for P10.

Figure 3:
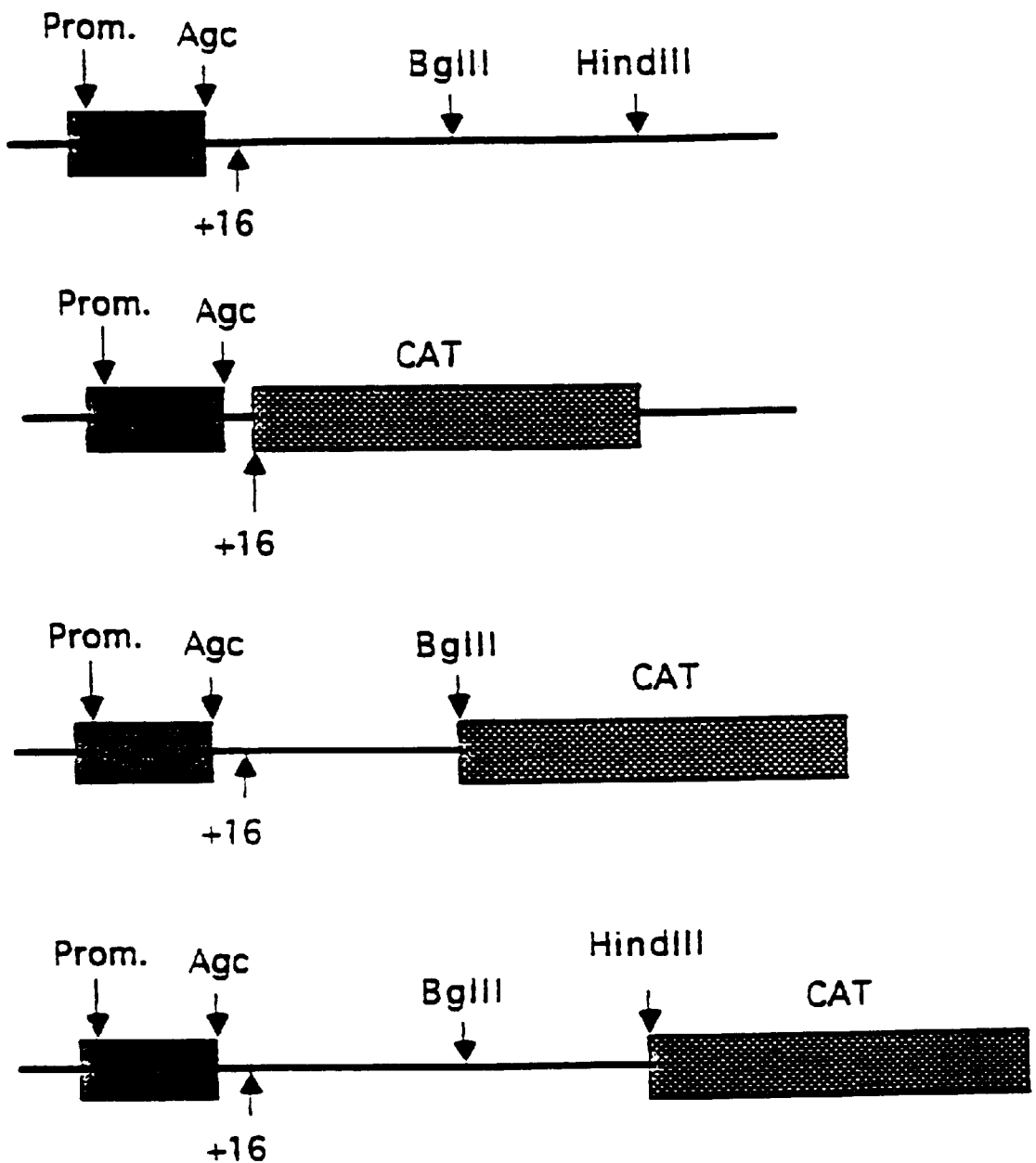
FIG. 3: illustration of the plasmid inserts pMH16, pMH150 and pMH230.

FIG. 3 depicts diagrammatically the inserts of plasmids pMH16, pMH150 and pMH230.

Plasmid pPH-RARα and pPH-RARγ

A 1518-bp KpnI-StuI fragment, or a 1564-bp NcoI-SmaI fragment, comprising the sequences in their entirety coding for the elements hPARα [PETROVITCH et al., Nature, vol. 330, pp. 444–450 (1987)] and hRARγ [BENBROOK et al., Nature, vol. 333, pp. 669–672 (1988)], respectively, were introduced downstream of the polyhedrin promoter into the SmaI site of the plasmid pGmAc34T [DAVRINCHE et al. Biochem. Biophys. Res. Com., vol 195, pp. 469–477].

Plasmid pRARα (P10) and pRARγ (P10)

In the same manner, the sequences coding for the hRAR elements were introduced at the BglII site of plasmid pMH16.

2) Obtaining of recombinant baculoviruses

For each of the transfer vectors described above, $4 \times 10^6$ Sf9 cells are cotransfected by lipofection (DOTAP, BOEHRINGER MANNHEIM) with 10 µg of vector and 1 µg of viral DNA.

Recombinations at the polyhedrin site are performed by cotransfecting the plasmid in question with wild-type AcMNPV virus DNA, while recombinations at the P10 site are performed by cotransfecting the plasmid in question with the DNA of a modified baculovirus (AcSLP10) in which the promoter and the polyhedrin gene have been excised and the sequence coding for polyhedrin put back under the control of the P10 promoter.

Two clones of each recombinant were purified independently.

Figure 4:
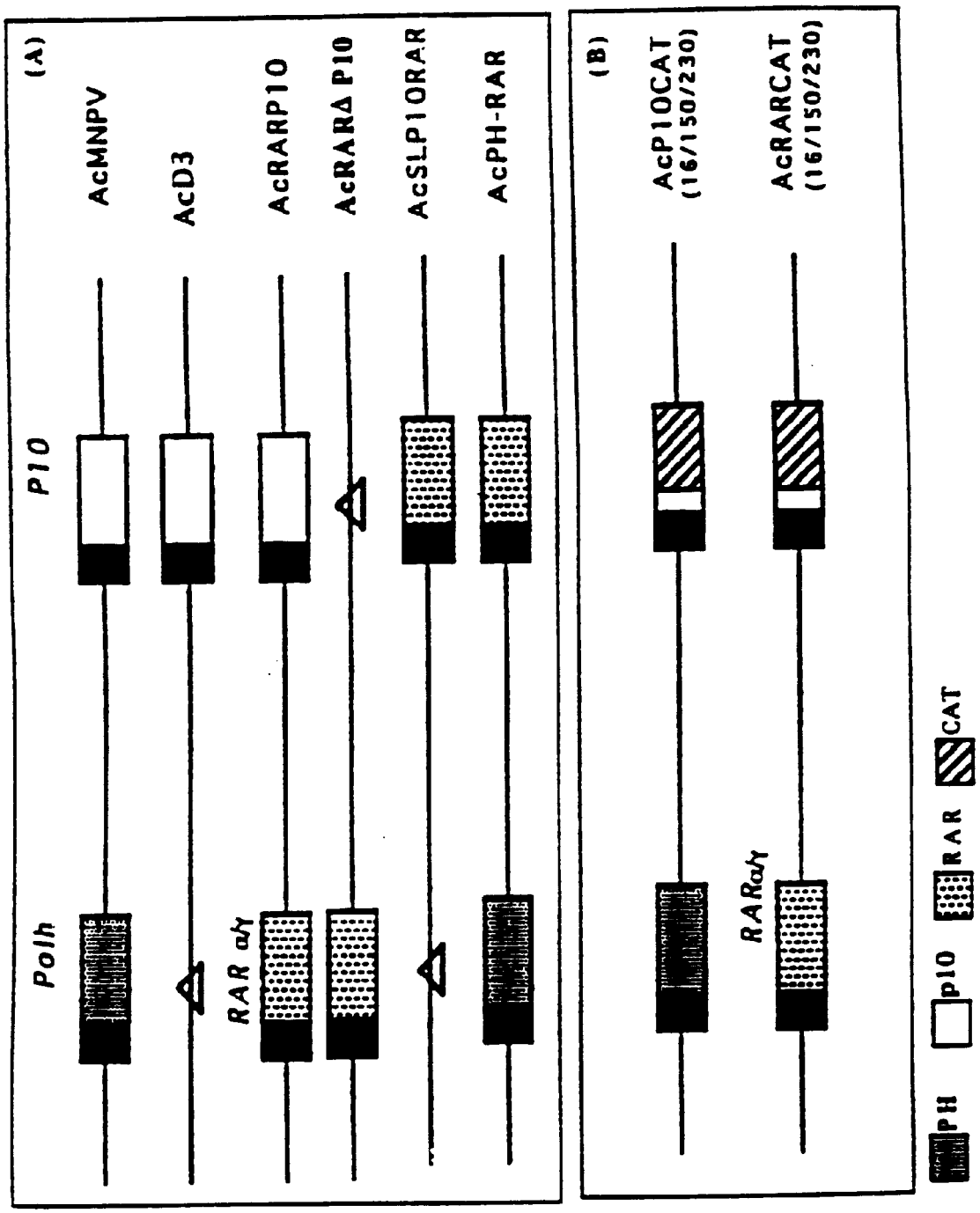
FIG. 4: (A) and (B), illustration of recombinant viruses.

FIG. 4 depicts diagrammatically the various recombinant viruses obtained. The promoters (P10 and polyhedrin) are represented by a solid black rectangle, the P10 sequence is represented by a completely clear rectangle, the sequence coding for polyhedrin is represented by a closely dotted rectangle (▦), the sequences coding for the RARs are represented by a more loosely dotted rectangle (▒) and the sequence coding for CAT is represented by a hatched rectangle.

FIG. 4A depicts, from top to bottom:

the wild-type AcMNPV virus;

a virus bereft of the polyhedrin promoter and gene (AcD3);

a virus obtained after recombination of a plasmid pPH-RAR with the wild-type virus DNA (AcRARP10);

a virus obtained after recombination of a plasmid pPH-RAR with the DNA of virus bereft of the P10 promoter and gene (AcRARΔP10);

a virus obtained after recombination of a plasmid pRAR (P10) with the DNA of virus bereft of the polyhedrin promoter (AcSLP10RAR);

a virus obtained after recombination of a plasmid pRAR (P10) with the wild-type virus DNA (AcPHRAR).

FIG. 4B depicts diagrammatically the recombinants carrying the CAT gene at different positions within the P10 sequence (+16, −150 and +230), and the RARα or γ gene at the polyhedrin locus:

- a virus obtained after recombination of one of the plasmids pMH16, pMH150 or pMH230 with the wild-type virus DNA (AcP10CAT);
- a virus obtained after recombination of a plasmid pPH-RAR with the virus AcP10CAT DNA (AcRARCAT); [sic]

EXAMPLE 2

EXPRESSION OF P10 IN THE RAR RECOMBINANTS

The cells (*Spodoptera frugiperda* Sf9) are maintained at 28° C. in TC100 medium (GIBCO/BRL) supplemented with 5% of heat-inactivated foetal calf serum.

The cells are infected with a viral suspension (wild-type AcMNPV or test recombinant) with a multiplicity of infection of 10 PFU (plage [sic] forming units) per cell. After one hour of adsorption, the viral inoculum is replaced by a fresh culture medium.

The cells infected with AcMNPV, AcRARαP10, AcRARγP10, AcRARαΔP10 and AcRARγΔP10, respectively, were harvested 48 hours after infection, washed in cold PBS buffer, then resuspended in sample buffer and brought to the boil for 5 min. The same preparation is performed on uninfected cells.

The total proteins of each preparation are analysed by SDS-PAGE on a 12% polyacrylamide gel. The gels are stained with Coomassie blue.

Comparison of the electrophoretic profiles of the total proteins of cells infected with the RAR recombinants (AcRARαP10 and AcRARγP10) with the electrophoretic profile of total proteins of cells infected with the wild-type AcMNPV baculovirus shows that a protein of apparent molecular weight 10 kDa is overproduced in the cells infected with the RAR recombinants. This overproduction is especially large in the cells infected with the recombinant AcRARγP10. The band of apparent molecular weight 10 kDa is not seen in the profile of the total proteins of cells infected with recombinants AcRARαΔP10 and AcRARγΔP10.

To verify whether the above observations reflect an increase in transcription of the P10 gene, the total cytoplasmic RNAs were isolated from the infected cells 48 h and 72 h after infection, and analysed by dot-blot hybridization using P32-labelled [sic] RNA probes complementary to the P10 and 39K sequences and obtained using the PROMEGA RIBOPROBE kit (PROMEGA, France).

Counting is carried out in a scintillation counter.

The results are illustrated in Table I below, which relates to the vectors depicted in FIGS. 4A and 4B.

TABLE I

| | cpm | | | |
|---|---|---|---|---|
| | P10 | | 39K | |
| Virus | 48 h | 72 h | 48 h | 72 h |
| None | 370 ± 10 | 1010 ± 40 | 390 ± 12 | 530 ± 25 |
| AcMNPV | 32900 ± 580 | 26290 ± 450 | 7390 ± 370 | 6050 ± 310 |

TABLE I-continued

| | cpm | | | |
|---|---|---|---|---|
| | P10 | | 39K | |
| Virus | 48 h | 72 h | 48 h | 72 h |
| AcD3 | 31450 ± 800 | 37970 ± 720 | 7580 ± 420 | 8520 ± 470 |
| RARα1 | 73920 ± 1300 | 96740 ± 880 | 8840 ± 450 | 11980 ± 630 |
| RARα2 | 79530 ± 1500 | 93120 ± 950 | 9810 ± 600 | 11500 ± 600 |
| RARΔp10 | 10950 ± 550 | 11200 ± 600 | 9550 ± 720 | 5770 ± 220 |
| RARγ1 | 98290 ± 1100 | 146230 ± 1200 | 5300 ± 350 | 5820 ± 280 |
| RARγ2 | 138090 ± 1450 | 142000 ± 1380 | 6080 ± 290 | 6400 ± 300 |

Examination of the mean values measured 48 h after infection reveals that the amount of P10 mRNA produced by the recombinants AcRARαP10 and AcRARγP10 is twice and four times as high, respectively, as that observed with the wild-type baculovirus or with the baculovirus AcD3 bereft of the polyhedrin promoter. The results obtained 72 hours after infection are very similar to those observed 48 hours after infection. At the same time, no significant difference is observed between the different vectors as regards the production of 39K mRNA, measured by way of an internal control.

EXAMPLE 3

EXPRESSION OF THE CAT REPORTER GENE UNDER THE CONTROL OF THE P10 PROMOTER

The baculoviruses AcP10CAT16, AcP10CAT150 and AcP10CAT230 contain the CAT reporter gene at position +16, +150 and +230, respectively, in the sequence coding for P10, and the gene coding for polyhedrin under the control of its own promoter; the baculoviruses AcRARαCAT16, AcRARγCAT16, AcRARαCAT150, AcRARγCAT150, AcRARαCAT230 and AcRARγCAT230 contain the CAT reporter gene at position +16, +150 and +230, respectively, in the sequence coding for P10, and, in addition, the gene coding for an α or γ retinoic acid receptor under the control of the polyhedrin promoter. These different vectors are obtained as described in Example 1 above.

The presence of the CAT protein and also CAT activity are tested for on the cell extracts prepared from Sf9 cells infected with these different vectors and harvested 48 hours after infection.

Expression of the CAT gene is determined after immunoelectrophoretic transfer: the total proteins are analysed by SDS-PAGE as described in Example 1 above and transferred onto a nitrocellulose membrane. CAT is detected with anti-CAT antibodies (5 PRIME>3 PRIME INC.), or by measurement of the CAT activity according to the standard method described by GORMAN et al. [Mol. Cell. Biol. No. 2, 1044–1051 (1982) [lacuna]. The acetylated forms of the substrate (Ac-CM) are separated from the native substrate (CM) by ascending thin-layer chromatography on silica.

In the case of cells infected with the vectors of type +150 and +230 and coexpressing a gene coding for an α or γ retinoic acid receptor, it is established by immunotransfer that, for the viruses AcRARαCAT150, AcRARγCAT150, AcRARαCAT230 and AcRARγCAT230, that there is a very marked increase in the signal corresponding to CAT relative to the viruses AcP10CAT150 and AcP10CAT230. The observed results are confirmed by the measurement of the CAT activity.

We claim:

1. A method for regulating the expression of a gene of interest, wherein said method comprises:
   a) providing an expression vector comprising a baculovirus promoter and a RARE-type DNA sequence situated in proximity thereof, and placing said gene of interest under the transcriptional control of said baculovirus promoter, and
   b) expressing said gene of interest in the presence of the translation product of a gene coding for a RAR-type hormone receptor.

2. A method according to claim 1, wherein said baculovirus promoter is the P10 promoter on the polh promoter.

3. A method according to claim 1, wherein said RAR-type hormone receptor is selected from the group consisting of RARα receptors, RARβ receptors and RARγ receptors.

4. A method according to claim 1, wherein said RARE-type DNA sequence has the sequence of SEQ ID NO: 1.

5. An expression vector, suitable for use in the method of claim 1, wherein said vector comprises:
   a) a first baculovirus promoter and a RARE-type DNA sequence situated in proximity thereof, and
   b) a second baculovirus promoter, and a DNA sequence coding for an RAR type hormone receptor, placed under the transcriptional control thereof.

6. An expression vector, wherein said vector comprises at least a baculovirus promoter and a RARE-type DNA sequence situated in proximity thereof, and
   i) said vector does not comprise the P10 promoter and the RARE-type DNA sequence GTTGACAGTGTTCA SEQ ID NO:2, in the same relative location as in the wild P10 gene, or
   ii) said vector does not comprise the P10 promoter and the RARE-type DNA sequence GTTGACAGTGTTCA SEQ ID NO:2 separated by the same sequence as in the wild P10 gene.

7. An expression vector according to claim 6, further comprising a gene of interest under transcriptional control of said baculovirus promoter.

8. An expression vector according to claim 6, further comprising at least one site for inserting a gene of interest under transcriptional control of said baculovirus promoter.

9. An expression vector according to claim 8, further comprising a gene of interest under transcriptional control of said first baculovirus promoter.

10. An expression vector according to claim 8, further comprising at least one site for inserting a gene of interest under transcriptional control of said baculovirus promoter.

11. An expression vector for expressing a gene of interest under the transcriptional control of the baculovirus polh promoter, wherein said vector comprises the whole sequence of the baculovirus polh promoter and of the baculovirus P10 promoter, and is devoid of RARE-type sequences in proximity to the P10 promoter.

12. An expression vector according to claim 11, which is devoid of the whole P10 coding sequence.

13. An expression vector of claim 11, further comprising at least one site for insertion of a gene of interest under transcriptional control of the polh promoter.

14. An expression vector of claim 11, further comprising a gene of interest under transcriptional control of the polh promoter.

* * * * *

UNITED STATES PATENT AND TRADEMARK OFFICE
CERTIFICATE OF CORRECTION

PATENT NO. : 5,939,285  
DATED : August 17, 1999  
INVENTOR(S) : Gérard Devauchelle et al.

It is certified that error appears in the above-identified patent and that said Letters Patent is hereby corrected as shown below:

<u>Title page,</u>
Item [75], Inventor, the first city should be -- Saint-Christol-les-Alès --.
Item [73], Assignee, should be -- Institut National de la Recherche Agronomique (INRA) --.
Item [86], PCT No.: should be -- PCT/FR96/00437 --.

Signed and Sealed this

Twenty-fifth Day of October, 2005

JON W. DUDAS
*Director of the United States Patent and Trademark Office*